United States Patent [19]

May, Jr.

[11] Patent Number: 5,458,570

[45] Date of Patent: Oct. 17, 1995

[54] ABSORBABLE CATHETER AND METHOD OF USING THE SAME

[76] Inventor: James W. May, Jr., P.O. Box 125, Lincoln, Mass. 01773

[21] Appl. No.: 180,378

[22] Filed: Jan. 12, 1994

Related U.S. Application Data

[62] Division of Ser. No. 43,155, Apr. 5, 1993, abandoned, which is a continuation of Ser. No. 644,218, Jan. 22, 1991, abandoned.

[51] Int. Cl.$^6$ .................................................. A61M 31/00
[52] U.S. Cl. ........................... 604/49; 604/28; 604/53; 604/265
[58] Field of Search ....................... 604/265, 264, 604/266, 272, 280, 28, 49, 52, 53; 606/230, 231, 198, 154

[56] References Cited

U.S. PATENT DOCUMENTS

| | | | |
|---|---|---|---|
| 2,092,512 | 9/1937 | Herrman et al. | 606/230 |
| 2,127,903 | 8/1938 | Bowen | 606/154 |
| 2,593,980 | 4/1952 | Calicchio | 604/265 |
| 3,886,947 | 6/1975 | Sawyer | 604/266 |
| 3,888,249 | 6/1975 | Spencer | 604/247 |
| 5,049,138 | 9/1991 | Chevalier et al. | 604/265 |
| 5,129,889 | 7/1992 | Hahn et al. | 604/265 |

*Primary Examiner*—C. Fred Rosenbaum
*Assistant Examiner*—V. Alexander
*Attorney, Agent, or Firm*—Pandiscio & Pandiscio

[57] ABSTRACT

A new and improved catheter is disclosed which comprises a tube-like body having a distal end and a proximal end, wherein at least the distal end of the catheter is formed out of a bioabsorbable material, whereby at least the distal end of the catheter will be naturally absorbed by the body after a predetermined period of time has passed so as to eliminated the need for a second, subsequent surgical procedure to remove at least the distal end of the catheter once it is no longer needed. The proximal end of the catheter may or may not be formed out of a bioabsorbable material, and the proximal end of the catheter may be adapted for positioning outside the body, or it may be adapted for positioning subcutaneously within the body.

5 Claims, 2 Drawing Sheets

DIRECTION OF BLOOD FLOW

ABSORBABLE CATHETER AND METHOD OF USING THE SAME

This is a division of U.S. application Ser. No. 08/043,155 filed Apr. 5, 1993 for 'Absorbable Catheter And Method of Using The Same' now abandoned, which is a File Wrapper Continuing Application of U.S. application Ser. No. 07/644,218 filed Jan. 22, 1991 for 'Absorbable Catheter And Method Of Using The Same', now abandoned.

FIELD OF THE INVENTION

This invention relates to medical devices in general, and more to particularly to catheters.

BACKGROUND OF THE INVENTION

In many medical procedures, it is necessary to introduce a fluid into the body. This fluid may be a relatively passive fluid, e.g. saline, or it may be a relatively active agent, e.g. an anticoagulant drug, an antibiotic drug, etc. Such fluids are typically introduced into the body by means of a catheter. Catheters generally comprise a tube-like body having a distal end for positioning inside the body at the point where the fluid is to be administered, and a proximal end for positioning outside the body so as to be readily accessible for the introduction of fluid into the catheter. In some circumstances the proximal end of the catheter may be placed subcutaneously near the outside of the body, where it may be accessed by a subcutaneous needle arrangement when fluid is to be delivered through the catheter.

In the case of active fluids such as anticoagulant drugs, the distal end of the catheter is traditionally positioned within a major artery or vein so that the fluid is introduced systemically into the entire body. However, in many cases it may be preferable to provide the active fluid to only a specific region of the body and not to the body as a whole. Thus, for example, in the case of anticoagulant drugs, catheters have been used to introduce anticoagulants at specific surgical sites so that the anticoagulant can be selectively applied to only the desired surgical site. In the case of anticancer drugs, catheters have been used to introduce powerful chemotherapy agents into the vessels or biliary tree of the liver for selective application to the cancerous area of the liver. In such cases, the catheter is implanted in the body so that its distal end is located in a specific region of the body where the active fluid is to be introduced, with the proximal end of the catheter being located in an easily-accessed position outside, or just inside, the body.

Unfortunately, since catheters have been traditionally formed out of a permanent, non-bioabsorbable material, emplacement of a catheter with its distal end deep within the body has traditionally required a second, subsequent surgical procedure to remove the catheter from its place in the body once it is no longer needed. This requirement of a second, subsequent surgical procedure has obvious disadvantages. This is particularly true if the catheter has been placed in an artery, since the subsequent removal of the catheter from the artery may cause further bleeding. In addition, the need for a second, subsequent surgical procedure to remove the catheter may make emplacement of the catheter in a deep, non-readily accessible portion of the body unacceptable in certain circumstances.

OBJECTS AND SUMMARY OF THE PRESENT INVENTION

Accordingly, one object of the present invention is to provide a new and improved catheter which is specifically adapted to have its distal end positioned deep within the body for the regional application of an active fluid and which does not suffer from the aforementioned disadvantages.

Another object of the present invention is to provide a new and improved catheter which would permit the distal end of the catheter to be located deep within the body for use in the regional administration of an active fluid and which would not require a second, subsequent surgical procedure to remove the catheter from its position within the body once it is no longer needed.

Still another object of the present invention is to provide an improved method of administering an active fluid deep within the body which does not suffer from the disadvantages associated with prior art methods and apparatus.

Yet another object of the present invention is to provide an improved method of administering an active fluid deep within the body which does not require a second, subsequent surgical procedure to remove a catheter from its position within the body once the catheter is no longer needed.

And another object is to provide an improved method of administering an active fluid into a blood vessel deep within the body which does not create additional problems of blood clotting due to the presence of a fluid-carrying catheter in the blood vessel.

These and other objects of the present invention are addressed by a new and improved catheter which comprises a tube-like body having a distal end and a proximal end, wherein at least the distal end of the catheter is formed out of a bioabsorbable material, whereby at least the distal end of the catheter will be naturally absorbed by the body after a predetermined period of time has passed so as to eliminate the need for a second, subsequent surgical procedure to remove at least the distal end of the catheter once it is no longer needed. In such catheters the proximal end of the catheter may or may not be formed out of a bioabsorbable material. In addition, the proximal end of the catheter may be adapted for positioning outside the body, or it may be adapted for positioning subcutaneously within the body. When a catheter must be used to administer an active fluid into a blood vessel deep within the body, the distal end of the catheter is emplaced in a small side branch vessel joining the target blood vessel so as to avoid causing blood clotting in the target vessel. Alternatively, the distal end of the catheter may be emplaced directly in the target blood vessel and blood clotting in the vessel avoided by using a catheter which has a sufficiently small diameter relative to the diameter of the blood vessel in which it is being implanted.

BRIEF DESCRIPTION OF THE DRAWINGS

Still other objects and features of the present invention will be more fully disclosed or rendered obvious in the following detailed description of the invention, which is to be considered together with the accompanying drawings wherein.

DETAILED DESCRIPTION OF THE INVENTION

Figure 1:
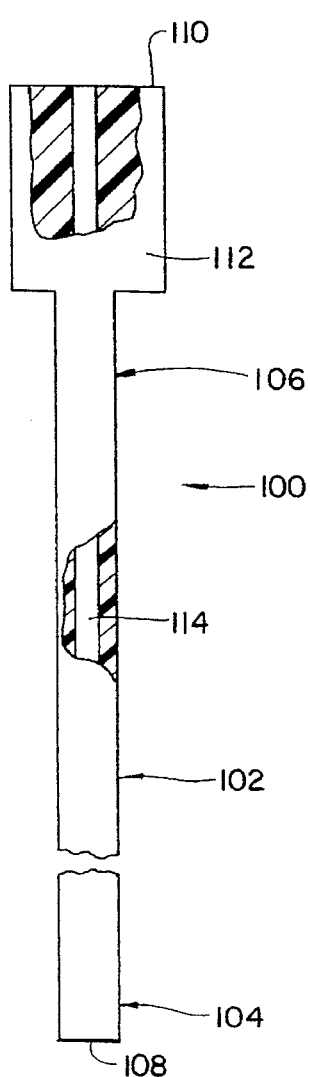
FIG. 1 is a side view of a first embodiment of the present invention.

Looking first at FIG. 1, there is shown a catheter 100 formed in accordance with the present invention.

Catheter 100 comprises a hollow tube-like body 102 formed from a somewhat flexible material and having a distal end 104 and a proximal end 106. Distal end 104 terminates in an end surface 108, and proximal end 106 terminates in an end surface 110. Preferably proximal end 106 is diametrically enlarged at 112 near its end surface 110 so as to provide a convenient fitting for connection with an appropriate fluid source, as is well known in the art. An interior passageway 114 extends for the length of the catheter, opening on distal end surface 108 and on proximal end surface 110.

On account of the foregoing construction, it will be appreciated that when catheter 100 is positioned within a body so that its distal end 104 is located at a surgical site and its proximal end 106 is located outside the body and is connected to an appropriate fluid source, the catheter will direct the fluid entering its distal end 106 to the surgical site adjacent its distal end 104 by means of its interior passageway 114.

To the extent just described, catheter 100 is substantially the same as any one of many different catheters in common use today.

Catheter 100 differs from prior art catheters in that at least the distal end 104 of the catheter is formed out of a bioabsorbable material, whereby at least that portion of the catheter will be naturally absorbed by the body after a predetermined period of time has passed.

More specifically, in the preferred embodiment, the entire catheter 100 is formed out of any one of the many bioabsorbable materials well known in the art. For example, the catheter 100 might be formed out of materials such as homo and copolymers of glycolide and trimethylene carbonate, homo and copolymers of lactide and glycolide, homo and copolymers of polylactic acid, or a blend of these homopolymers and copolymers. The catheter might also be coated with longer lasting materials, e.g. caprolactone and glycolide homo and copolymers, or glycolide and lactide homo and copolymers. Of course, the exact composition of such absorbable catheters will vary according to the absorption and flexibility characteristics desired. Such compositions are well known to persons skilled in the art.

By virtue of the foregoing construction, it will be appreciated that when catheter 100 is positioned within a body so that its distal end 104 is located at a surgical site and its proximal end 106 is located outside the body and is connected to an appropriate fluid source, the catheter will direct the fluid entering its proximal end 106 to the surgical site adjacent its distal end 104 by means of its interior passageway 114. In addition, inasmuch as catheter 100 is formed out of a bioabsorbable material, the catheter will be naturally absorbed by the body after a predetermined period of time has passed. Thus, it will be appreciated that the present catheter is ideally suited for use in those situations where the distal end of the catheter must be located deep within the body for use in the regional administration of an active fluid and where it would be impractical or undesirable to conduct a second, subsequent operation to remove the catheter once it is no longer needed.

In fact, the absorbable nature of the present catheter is such that in many situations an absorbable catheter might be routinely put in place during an operation as a purely prophylactic measure; then, if the patient's condition requires it, the catheter will be available as needed to deliver fluids to the surgical site; if, however, the patient's condition never requires it, the catheter is never activated. In any case, due to the fact that the catheter is formed out of bioabsorbable material, the catheter is always absorbed by the body after some predetermined period of time has passed, so that no second, subsequent operation is needed to remove the catheter once it is no longer needed.

It will be appreciated that it is not necessary for the entire catheter to be formed out of a bioabsorbable material; it is also contemplated that only the distal end of the catheter might be formed out of the bioabsorbable material, with the remainder of the catheter being formed out of non-bioabsorbable material. Of course, with such a construction, only that portion of the catheter which is formed out of bioabsorbable material will be naturally absorbed by the body after a predetermined period of time has passed; the remainder of the catheter will remain intact and may have to be physically removed from the body in a subsequent operation if it is disposed within the body.

Figure 2:
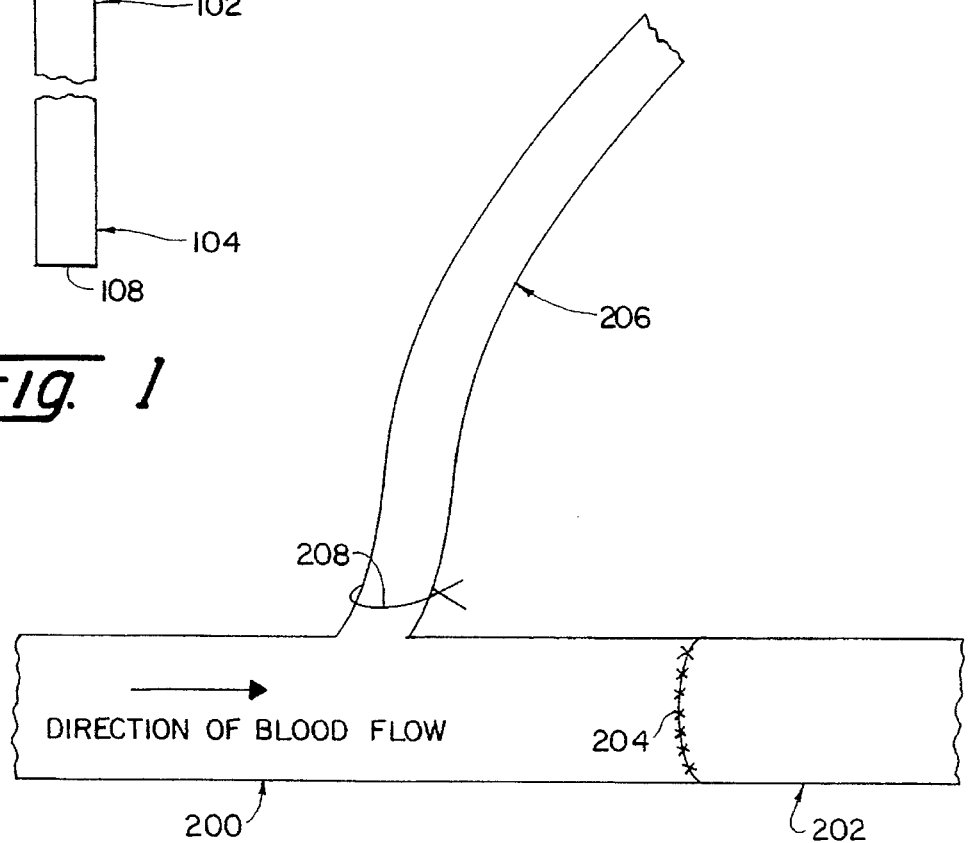
FIG. 2 is a schematic view showing a typical environment in which the catheter which comprises the present invention might be used.

Looking next at FIG. 2, there is shown a typical environment in which catheter 100 might be used. More. specifically, there is shown a main blood vessel 200 to which has been joined a graft vessel 202. In this circumstance there may be a concern of significant thrombosis occurring at the anastamosis line 204. However, the situation may also be such that systemic application of anticoagulants is undesirable. Thus, localized application of anticoagulants to the anastamosis line 204 might be indicated. The absorbable nature of catheter 100 would make it possible to supply the anticoagulants to the necessary location without requiring a second, subsequent operation to remove the catheter once the fear of thrombosis has passed.

Figure 3:
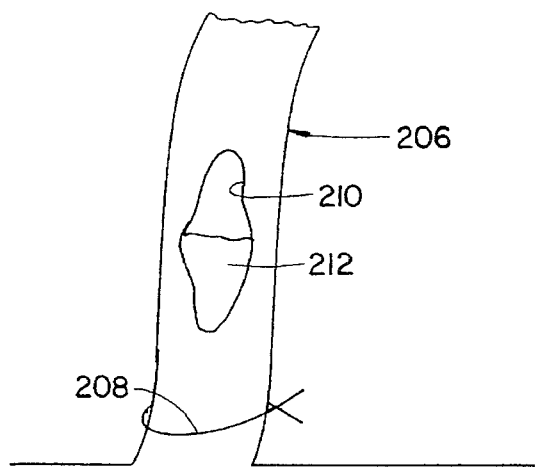
FIG. 3 is a schematic view showing in more detail the manner of forming an incision in a blood vessel which is to receive the distal end of the catheter which comprises the present invention.
Figure 4:
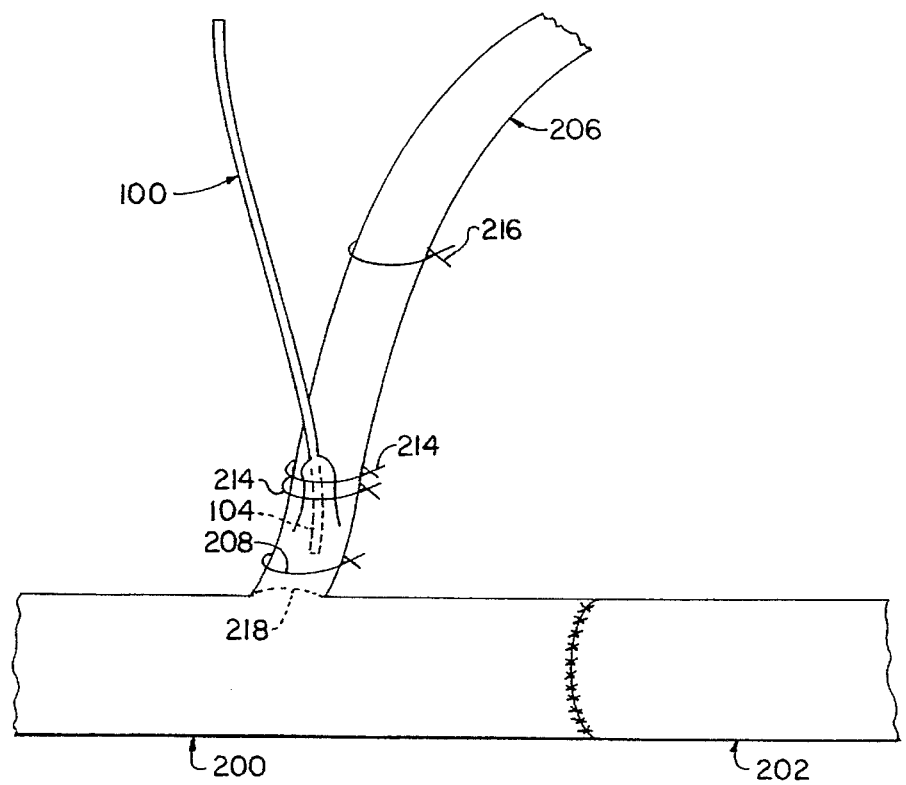
FIG. 4 is a schematic view showing the catheter of FIG. 1 emplaced in the environment of FIG. 2.

In such a circumstance, the surgeon would put catheter 100 in position adjacent the anastamosis line 204 at the time the graft 202 is put in position. This is done by selecting a side branch vessel 206 which is just upstream of the anastamosis line. The side branch vessel 206 is tied off at 208 adjacent where it joins the main vessel 200 so as to stop the flow of blood into the side branch vessel. Then an oblique incision 210 is formed in the side wall of the side branch vessel as shown in FIG. 3, whereby a flap portion 212 of the side wall may be pulled away from the side branch vessel so as to permit access to the interior of the side branch vessel. Then the catheter 100 is emplaced at the surgical site by threading its distal end 104 into the interior of the side branch vessel 206 via the incision 210, as shown in FIG. 4. As this is done, the portion of the catheter emerging from incision 210 is positioned parallel to the side branch vessel for at least a short distance, and the remainder of the catheter is brought up to the surface of the skin, where the proximal end of the catheter is attached to the skin so as to hold that portion of the catheter securely in place. The distal end of the catheter is made fast in the side branch vessel 206 by pulling flap portion 212 back up around the catheter and tying it in place with one or more suture ties 214. In addition, the flap portion 212 may be sutured to the surrounding wall of side branch vessel 206 adjacent the distal end of the catheter to provide a fluid-tight seal between the side branch vessel and the catheter.

In addition to the foregoing, the side branch vessel 206 is also tied off with a tie 216 further downstream from the juncture between the catheter 100 and the side branch vessel 206. Then the tie 208 at the joinder of the main vessel 200 and the side branch vessel 206 is released so as to restore blood flow back into the side branch vessel, and so as to allow the distal end of catheter 100 to communicate with artery 200. Then catheter 100 is irrigated (via its proximal end 106 located outside the body) with a simple saline solution or an anticoagulant solution so as to prevent blood from entering the interior of the catheter. Preferably the flow of irrigating fluid into the catheter is such that the portion of the side branch vessel located between catheter 100 and main vessel 200 will also be flushed with the irrigating fluid. This will help prevent any clotting from occurring in either the catheter body itself or in that portion of the side branch vessel located between catheter 100 and main vessel 200.

Thereafter, the primary incision to the surgical site may be closed, with the catheter remaining in place as previously described and with suture tie 216 still in place. Catheter 100 may then be periodically flushed with irrigating fluid as needed to prevent any clotting from occurring in either the catheter body or in that portion of the side branch vessel 206 connecting the catheter with main vessel 200.

If and when it is desired to introduce pharmacologic agents, e.g. anticoagulating drugs, to the anastamosis line 204, such agents may be quickly and easily introduced to the anastomosis line by introducing the pharmacologic agents to the proximal end 106 of the catheter which is located outside the body at the skin's surface; the agents will then flow down the catheter to the distal end of the catheter, into that portion of the side branch vessel 206 connecting the distal end of the catheter with main vessel 200, and then down the main vessel 200 to the anastamosis line 204.

It is to be appreciated that inasmuch as catheter 100 is formed out of a bioabsorbable material, the catheter will be naturally absorbed by the body after a predetermined period of time has passed, with no further action being required by the physician.

More preferably, however, when it is concluded that it is no longer necessary to have a catheter portal to the anastomosis line, any ongoing irrigation of the catheter is ceased and blood is drawn back up into the catheter. This will cause the side branch vessel 206 to seal at 218 with a slight dimple effect extending into the side branch vessel. Thereafter, the bioabsorbable nature of the catheter will cause the catheter to be naturally absorbed by the body, thereby eliminating the need for a second, subsequent surgical procedure to remove the catheter from the body.

In the foregoing description of the invention, it was indicated that a common application for catheter 100 might be to use the catheter 100 to introduce fluid into a main blood vessel 200, and it was indicated that, to this end, the distal end of the catheter should be emplaced in an adjacent side branch vessel 206 communicating with main blood vessel 200 rather than emplacing the catheter directly into main blood vessel 200. This technique of emplacing the catheter 100 into side branch vessel 206 rather than directly into main blood vessel 200 was disclosed inasmuch as placing a catheter directly into a main blood vessel can result in the occurrence of undesired blood clotting due to the presence of the catheter in the blood vessel.

More specifically, placement of the catheter into the side branch of the parent feeding vessel offers vascular access to fluid installation into the parent feeding vessel. When the catheter is no longer infused, blood is allowed to fill the side branch and the catheter, and with stagnation thrombosis of the side branch and catheter occurs. This thrombotic process, however, does not extend into the parent feeding vessel. This unique phenomenon allows placement of an absorbable—or non-absorbable—catheter without fear of parent feeding vessel thrombosis when the side branch vessel and catheter are ultimately allowed to thrombose.

In essence, I have found that cannulation into a side branch vessel will avoid thrombosis in the parent vessel which is the target of the cannulation.

Figure 5:
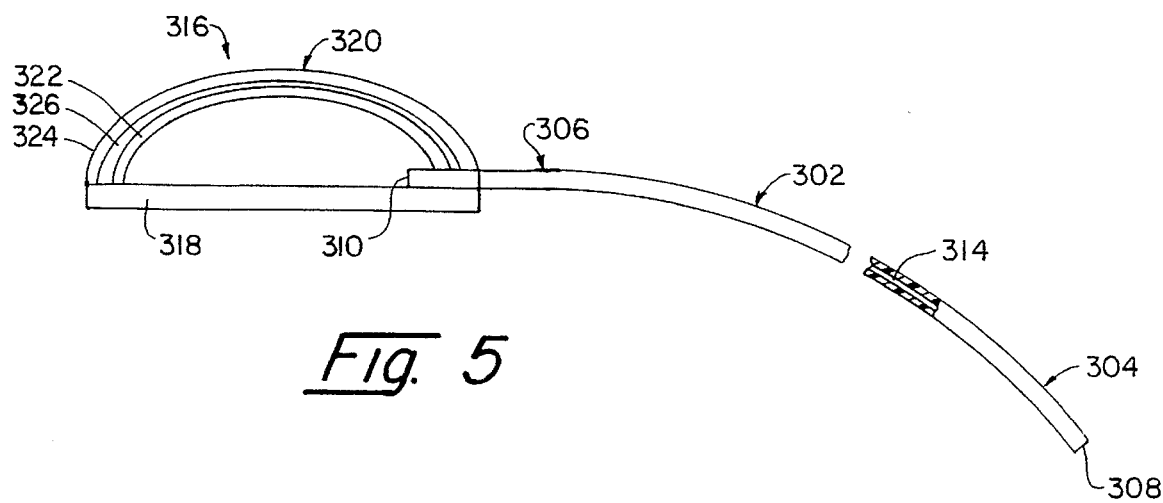
FIG. 5 discloses a second embodiment of the present invention.

Looking next at FIG. 5, there is shown a catheter 300 which comprises a second embodiment of the present invention.

Catheter 300 is intended to have both its distal and proximal ends emplanted inside the body, unlike the aforementioned catheter 100, which is intended to have its distal end implanted inside the body and its proximal end positioned outside the body. To this end, catheter 300 comprises a hollow tube-like body 302 formed from a somewhat flexible material and having a distal end 304 and a proximal end 306. Distal end 304 terminates in an end surface 308, and proximal end 306 terminates in an end surface 310. An interior passageway 314 extends for the length of tube-like body 302, opening on both distal end surface 308 and proximal end surface 310. At least the distal end 304 of tube-like body 302, and preferably the entire tube-like body 302, is formed out of a bioabsorbable material such as those previously disclosed and well known to those skilled in the art. Of course, the exact composition of tube-like body 302 will vary according to the absorption and flexibility characteristics desired for tube-like body 302.

A subcutaneous needle fitting 316 is disposed about the proximal end of body 302. Fitting 316 is of the sort well known in the art and comprises a metal base plate 318 and a silicon dome 320. Dome 320 comprises an inner silicon layer 322, an outer silicon layer 324, and a self-sealing gel 326 sandwiched between inner layer 322 and outer layer 324. Elements 322, 324 and 326 together comprise a self-sealing dome which can be punctured by a sharp needle and which will seal itself after being punctured by a needle. Needle fitting 316 is hollow, and the proximal end 306 of tube-like body 302 is connected to needle fitting 316 such that the hollow interior of the needle fitting communicates with the hollow interior of body 302.

In use, catheter 300 would have its distal end 304 positioned in the body in exactly the same way that the distal end of catheter 100 is positioned in the body. However, the proximal end of catheter 300 is positioned in the body so that needle fitting 316 is emplaced subcutaneously, i.e., below the surface of the skin, with metal base plate 318 extending substantially parallel to the surface of the skin. Thereafter, when it is desired to introduce fluids into the catheter, a needle is forced through dome 320 so that the needle enters the interior of the needle fitting 316 and strikes metal base plate 318. Base plate 318 will prevent further pentration of the needle, thereby insuring that the needle is properly located in the hollow interior of the needle fitting and simultaneously advising the physician of the same. Fluids may then be introduced into the interior of needle fitting 316 via the needle so that the fluids will thereafter run down the catheter to the desired location at the surgical site.

Since at least the distal end 304 of tube-like body 302, and preferably the entire tube-like body 302, is formed out a bioabsorbable material, it will be naturally absorbed by the body after a predetermined period of time has passed. However, since needle fitting 316 is not formed out of a bioabsorbable material, it will of course not be naturally absorbed by the body after a predetermined period of time has passed. Rather, it will have to be removed from the body with a subsequent surgical procedure. However, since the catheter's nonabsorbable needle fitting 316 is located fairly close to the skin's surface and is not located deep at the surgical site, the procedure to remove the nonabsorbable needle fitting 316 is a simple, minor surgical procedure which can be done under local anesthesia.

In the foregoing description of the invention, it was indicated that a common application for catheter 100 might be to use the catheter 100 to introduce fluid into a main blood vessel 200, and it was indicated that, to this end, the distal end of the catheter should be emplaced in an adjacent side branch vessel 206 communicating with main blood vessel 200 rather than emplacing the catheter directly into main blood vessel 200. This technique of emplacing the catheter 100 into side branch vessel 206 rather than directly into main blood vessel 200 was disclosed inasmuch as placing a catheter directly into a main blood vessel can result in the occurrence of undesired blood clotting due to the presence of the catheter in the blood vessel. However, experience has also shown that finding a suitable, well-situated side branch vessel can often be difficult.

In this respect, I have made a further discovery which affects not only the use of the absorbable catheters disclosed herein, but which also affects the use of conventional non-absorbable catheters as well. More particularly, I have found that a catheter may be emplaced directly into a main blood vessel without causing the aforementioned blood clotting so long as the catheter is carefully sized relative to the blood vessel in which it is emplaced. I have found that for a blood vessel of a given diameter, no clotting will occur so long as the diameter of the catheter does not exceed a particular threshold size; however, when the diameter of the catheter does exceed the particular threshold size for that blood vessel, the probability of clotting will increase as the catheter size increases. In addition, I have also found that as the size of the blood vessel increases, proportionately larger diameter catheters can be used without causing the occurrence of blood clotting. For example, I have found that for a small blood vessel of the type having a diameter of approximately 3 mm or less, the catheter should have a diameter less than about 20% of the diameter of the blood vessel so as to avoid clotting, whereas with a large blood vessel of the type having a diameter of approximately 1 cm or more, the catheter may have a diameter as large as about 33% of the diameter of the blood vessel without causing clotting.

It should be noted that the foregoing discovery of the relationship between catheter size, blood vessel size and blood clotting holds true regardless of whether the catheter involved is formed out of an absorbable material or anonabsorbable material.

Since certain changes may be made in the above apparatus and methods without departing from the scope of the present invention herein involved, it is intended that all matter contained in the foregoing description or shown in the accompanying drawings shall be interpreted in an illustrative and not a limiting sense.

ADVANTAGES OF THE INVENTION

Numerous advantages are achieved by using the present invention.

For one thing, a new and improved catheter is disclosed which is specifically adapted to have its distal end positioned deep within the body for the regional application of an active fluid and which does not suffer from the aforementioned disadvantages associated with prior art catheters.

In addition, a new and improved catheter is disclosed which would permit the distal end of the catheter to be located deep within the body for use in the regional administration of an active fluid and which would not require a second, subsequent surgical procedure to remove the catheter from its position within the body once it is no longer needed.

Also, an improved method is disclosed for administering an active fluid deep within the body which does not suffer from the disadvantages associated with prior art methods and apparatus.

Furthermore, an improved method is disclosed for administering an active fluid deep within the body which does not require a second, subsequent surgical procedure to remove a catheter from its position within the body once the catheter is no longer needed.

And an improved method is disclosed for administering an active fluid into a blood vessel deep within the body which does not create additional problems of blood clotting due to the presence of a fluid-carrying catheter in the blood vessel.

What is claimed is:

1. A method for delivering a fluid to a surgical site in a human or animal body, wherein said surgical site is located downstream of a main blood vessel, said method comprising the steps of:

(1) providing a catheter comprising an elongated hollow tube having a distal end and a proximal end, wherein at least the distal end of said tube is formed out of a bioabsorbable material;

(2) selecting a side branch blood vessel which is connected to said main blood vessel upstream of said surgical site;

(3) tying off said side branch blood vessel adjacent to said main blood vessel so as to stop the flow of blood into said side branch blood vessel;

(4) forming an incision in a side wall of said side branch blood vessel whereby a flap portion of said side wall may be pulled away from said side branch blood vessel so as to permit access to the interior of said side branch blood vessel;

(5) positioning said catheter so that said distal end of said tube extends into and communicates with said interior of said side branch blood vessel through said incision;

p1 (6) positioning said catheter so that (i) the portion of said catheter emerging from said incision extends adjacent to said side branch blood vessel for at least a short distance, and (ii) said proximal end of said catheter is positioned at and securely attached to the surface of the skin;

(7) pulling said flap portion back up around said distal end of said catheter and affixing said flap portion in place so that said distal end of said catheter is made fast in said side branch blood vessel;

(8) untying said side branch blood vessel so as to return the flow of blood into said side branch blood vessel;

(9) introducing a fluid to said proximal end of said tube so that said fluid will flow through said catheter to said side branch blood vessel and thereafter into said main blood vessel so as to reach said surgical site;

(10) ceasing said fluid flow through said catheter; and

(11) leaving said catheter in said human or animal body so that at least said distal end of said catheter will be naturally absorbed by said human or animal body after a predetermined period of time has passed.

2. A method according to claim 1 wherein, in Step (7), said flap portion is tied in place.

3. A method according to claim 1 wherein, in Step (7), said flap portion is sutured in place.

4. A method according to claim 1 wherein the following step is interposed between Step (10) and Step (11):

(10a) filling said side branch blood vessel and said distal end of said catheter with blood from said main blood vessel so that thrombosis occurs in both said side branch blood vessel and said catheter, whereby said side branch blood vessel will be sealed off from said main blood vessel, with a slight dimple extending into said side branch blood vessel.

5. A method for introducing fluid into a main blood vessel without causing the occurrence of blood clotting therein, said method comprising the steps of:

(1) providing a catheter comprising an elongated hollow tube having a distal end and a proximal end, wherein at least the distal end of said tube is formed out of a bioabsorbable material;

(2) selecting a side branch blood vessel which is connected to and fed by said main blood vessel;

(3) inserting said distal end of said tube into said side branch blood vessel so that the interior of said tube communicates with the interior of said side branch blood vessel;

(4) introducing fluid into said proximal end of said tube so that said fluid flows through said tube, into said side branch blood vessel and into said main blood vessel (5) ceasing said fluid flow through said tube;

(6) filling said side branch blood vessel and said distal end of said catheter with blood so that thrombosis occurs in both said side branch blood vessel and said distal end of said catheter; and (7) leaving said catheter in said human or animal body so that at least said distal end of said catheter will be naturally absorbed by said human or animal body after a predetermined period of time has passed.

\* \* \* \* \*